(12) United States Patent
Huang

(10) Patent No.: US 10,617,769 B2
(45) Date of Patent: Apr. 14, 2020

(54) BACTERIUM-CONTAINED HYDROGEL AND METHOD OF MAKING THE SAME

(71) Applicant: TCI Co., Ltd., Taipei (TW)

(72) Inventor: Chun-Ming Huang, Taoyuan (TW)

(73) Assignee: TCI Co., Ltd., Taipei (TW)

(*) Notice: Subject to any disclaimer, the term of this patent is extended or adjusted under 35 U.S.C. 154(b) by 88 days.

(21) Appl. No.: 15/655,915

(22) Filed: Jul. 21, 2017

(65) Prior Publication Data

US 2018/0021452 A1 Jan. 25, 2018

Related U.S. Application Data

(60) Provisional application No. 62/365,392, filed on Jul. 22, 2016.

(51) Int. Cl.
*A61K 47/69* (2017.01)
*A61K 47/34* (2017.01)
(Continued)

(52) U.S. Cl.
CPC ........ *A61K 47/6903* (2017.08); *A61K 9/0014* (2013.01); *A61K 9/06* (2013.01);
(Continued)

(58) Field of Classification Search
CPC ............ A61K 2300/00; A61K 31/7036; A61K 31/555; A61K 31/295; A61K 45/06; A61K 2008/58; A61K 31/00; A61K 8/19; A61K 8/361; A61K 8/365; A61K 8/368; A61K 8/41; A61K 31/197; A61K 31/198; A61K 35/66; A61K 47/34; A61K 47/6903; A61K 9/0014; A61K 9/06; A61K 9/7023; A61K 35/744; A61K 35/745; A61K 35/747; A61K 35/74; A61K 36/06; A61K 47/10; A61K 9/0024; A61K 9/7007; A61K 31/575; A61K 9/0031; A61K 9/0053; A01N 59/16; A01N 37/36; A01N 37/44; A01N 37/38; A01N 37/42; A01N 43/40; A01N 37/10; A01N 55/02; A23K 20/30; A23K 50/75; A23K 20/20; A23K 50/10; A23K 50/30; A23K 20/195; A23K 50/60; A23K 20/10; A23V 2002/00; C07F 15/025; C09D 5/14; A01K 14/00; A01K 43/00; A01K 45/005; A01K 67/00; A22C 18/00; A22C 21/00; A23L 2/52; A23L 33/165; A23L 33/127; A23L 33/16; A61Q 11/00; A61Q 17/005; A61L 12/08; A61L 2202/24; A61L 2/0088; A61L 2/16; A61L 2/18; A61L 2/22; A61L 15/36; A61L 15/60; G02B 1/043; A61P 31/04; A61P 1/04; C12R 1/45; C12R 1/01; C08L 2666/02; C08L 51/003; C08L 51/08; C08L 53/00; C04B 16/0683; C04B 28/02; C04B 22/085; C04B 24/04; C04B 24/08; C04B 24/10; C04B 24/123; C04B 2103/0001; C04B 2103/0072; C04B 16/06; C04B 24/00; C04B 14/06; C04B 14/28; C04B 16/0625; C04B 16/0633; C04B 16/0641; C04B 16/0691; C04B 18/08; C04B 18/141; C04B 2111/343; C12N 11/04; C12N 1/20; C12N 1/04; C12N 1/02; D01F 1/10; D01F 11/08; D01F 6/66; C02F 3/108; C02F 3/00; C02F 3/34; C02F 2103/001; C02F 2103/002; C02F 2103/005; C02F 2103/20; C02F 2103/26; C02F 2203/006; C02F 2303/10; C02F 3/102; C02F 3/109; C02F 3/341; C02F 3/348; Y02W 10/15; Y02W 10/30; B09C 1/10; B09C 1/002;
(Continued)

(56) References Cited

U.S. PATENT DOCUMENTS 7,419,593 B2* 9/2008 Trauger .................. B09C 1/002
156/62.2
8,682,619 B2* 3/2014 Amodei ............... A61K 9/0024
703/1
(Continued)

FOREIGN PATENT DOCUMENTS

CN 103327966 A 9/2013
CN 103230619 B 11/2014
(Continued)

OTHER PUBLICATIONS

Shu et al, "Fermentation of Propionibacterium acnes, a Commensal Bacterium in the Human Skin Microbiome, as Skin Probiotics against Methicillin-Resistant *Staphylococcus aureus*", PLOS ONE, Published: Feb. 6, 2013; https://doi.org/10.1371/journal.pone.0055380.*
Peter Krsko et al., "Biointeractive hydrogels," Materials Today, vol. 8, No. 12, pp. 36-44, Dec. 2005.
Ming-Shan Kao et al."The mPEG-PCL Copolymer for Selective Fermentation of *Staphylococcus lugdunensis* Against Candida parapsilosis in the Human Microbiome," J Microb Biochem Technol., Published online on Jun. 19, 2016.
(Continued)

*Primary Examiner* — Deborah K Ware
(74) *Attorney, Agent, or Firm* — CKC & Partners Co., LLC

(57) ABSTRACT

The present disclosure provides a bacterium-contained hydrogel including: hydrogel, bacteria, and metabolites. The hydrogel includes a plurality of polymer chains crosslinked with each other, and each of the polymer chains include at least one polyethylene glycol chain. The bacteria are located in the hydrogel, and the bacteria use the polymer chains as a carbon source for fermentation. The metabolites are produced from the fermentation of the bacteria using the polymer chains as a carbon source. The metabolites distribute in the hydrogel. The present disclosure also provides a method for making bacterium-contained hydrogel.

10 Claims, 9 Drawing Sheets

(51) Int. Cl.
    *A61K 9/06*         (2006.01)
    *A61K 35/66*       (2015.01)
    *A61L 15/60*       (2006.01)
    *A61K 9/00*         (2006.01)
    *A61P 31/04*       (2006.01)
    *A61L 15/36*       (2006.01)
    *C12R 1/45*        (2006.01)
    *A61K 9/70*         (2006.01)

(52) U.S. Cl.
    CPC .............. *A61K 35/66* (2013.01); *A61K 47/34* (2013.01); *A61L 15/36* (2013.01); *A61L 15/60* (2013.01); *A61P 31/04* (2018.01); *C12R 1/45* (2013.01); *A61K 9/7023* (2013.01)

(58) Field of Classification Search
    CPC .... C08F 283/00; C08F 289/00; C08F 290/06; C08F 290/061; C12Q 1/02; D01D 5/003; D01D 5/0007; G01N 2520/00; Y10T 428/249921; Y10T 428/268; B32B 27/12; B32B 33/00; B32B 5/26; D04H 1/407; D04H 1/413; D06N 2205/04; D06N 2211/16; D06N 3/0011; D06N 3/045; D06N 3/123; D06N 3/125; E02B 15/04; E02D 31/004; E02D 3/00; Y10S 210/901; C09K 8/582; C09K 8/584; C12M 21/04; C12M 23/20; C12M 23/24; C12M 23/40; C12M 25/02; E21B 43/16; E21B 43/24; Y02A 50/47; Y02E 50/343; G01Q 60/32; G01Q 10/00; G01Q 10/02; G01Q 10/04; G01Q 40/00; B82Y 35/00; G01B 17/08
    See application file for complete search history.

(56) References Cited

U.S. PATENT DOCUMENTS

| | | | | |
|---|---|---|---|---|
| 8,734,823 | B2* | 5/2014 | Amodei | A61K 9/0024 |
| | | | | 424/422 |
| 10,093,579 | B2* | 10/2018 | Jonkers | C04B 24/123 |
| 2003/0175824 | A1 | 9/2003 | Pishko et al. | |
| 2004/0258723 | A1* | 12/2004 | Singh | A61C 19/063 |
| | | | | 424/401 |
| 2006/0000767 | A1* | 1/2006 | Trauger | B09C 1/002 |
| | | | | 210/503 |
| 2009/0258051 | A1* | 10/2009 | Chidambaram | A61K 9/0024 |
| | | | | 424/423 |
| 2010/0120127 | A1* | 5/2010 | O'Mahony | C12N 1/02 |
| | | | | 435/261 |
| 2010/0143447 | A1* | 6/2010 | Hansen | A61L 15/36 |
| | | | | 424/445 |
| 2012/0107900 | A1* | 5/2012 | Greiner | C12N 1/04 |
| | | | | 435/179 |
| 2014/0017921 | A1* | 1/2014 | Hsu | H01R 24/60 |
| | | | | 439/166 |
| 2018/0147221 | A1* | 5/2018 | von Maltzahn | A61K 45/06 |
| 2018/0235987 | A1* | 8/2018 | von Maltzahn | A61K 45/06 |
| 2018/0296582 | A1* | 10/2018 | von Maltzahn | A61K 45/06 |

FOREIGN PATENT DOCUMENTS

| | | |
|---|---|---|
| TW | 546149 B | 8/2003 |
| TW | 201530119 A | 8/2015 |

OTHER PUBLICATIONS

Thomas P. Kraehenbuehl et al., "Three-dimensional extracellular matrix-directed cardioprogenitor differentiation: systematic modulation of a synthetic cell-responsive PEG-hydrogel", Biomaterials 29 (2008), pp. 2757-2766.

Peter Krsko et al., "Spatially controlled bacterial adhesion using surface-patterned poly(ethylene glycol) hydrogels", Acta Biomaterialia 5 (2009) pp. 589-596, 2009.

Dr. Edward A. Phelps et al., "Maleimide cross-linked bioactive PEG hydrogel exhibits improved reaction kinetics and cross-linking for cell encapsulation and in-situ delivery", Adv Mater. 24(1), Jan. 3, 2012, 12 pages.

G. P. Raeber et al., "Molecularly Engineered PEG Hydrogels: A Novel Model System for Proteolytically Mediated Cell Migration", Biophysical Journal vol. 89, pp. 1374-1388, Aug. 2005.

Airong Song et al., "Antibacterial and Cell-Adhesive Polypeptide and Poly(ethylene glycol) Hydrogel as a Potential Scaffold for Wound Healing", Acta Biomater. 8(1): 41-50, Jan. 2012, 24 pages.

* cited by examiner

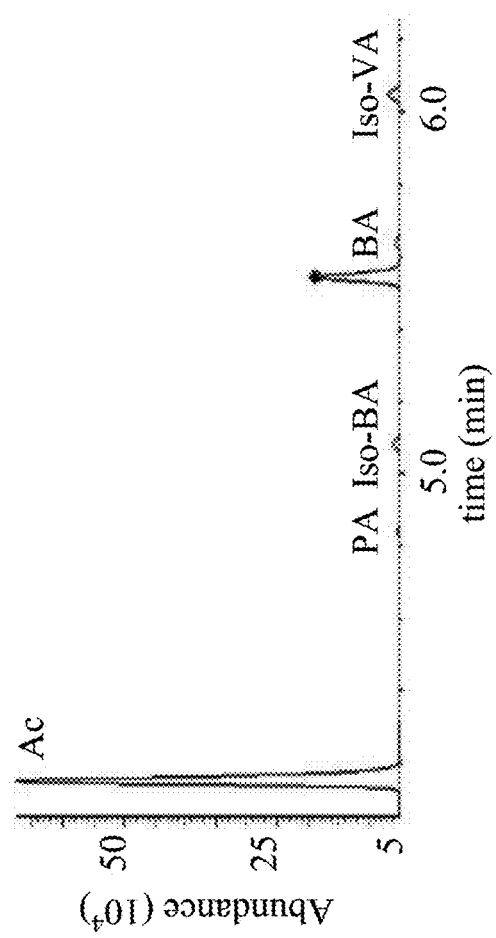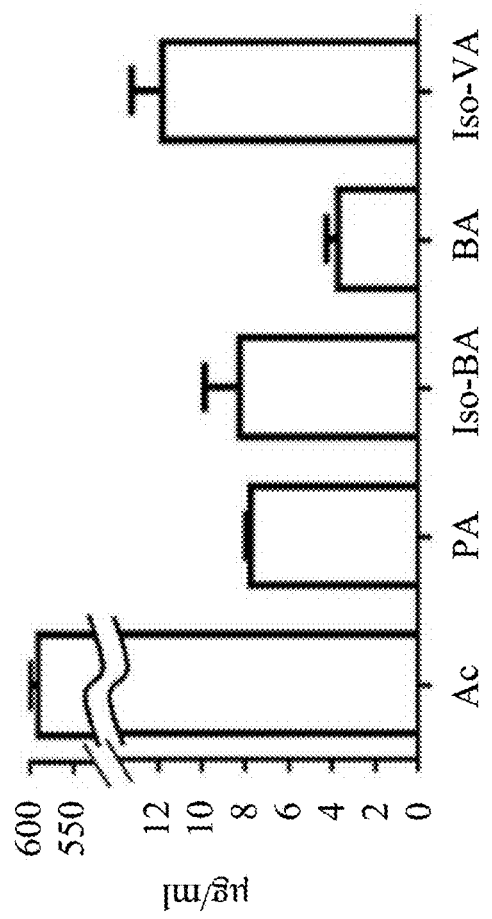

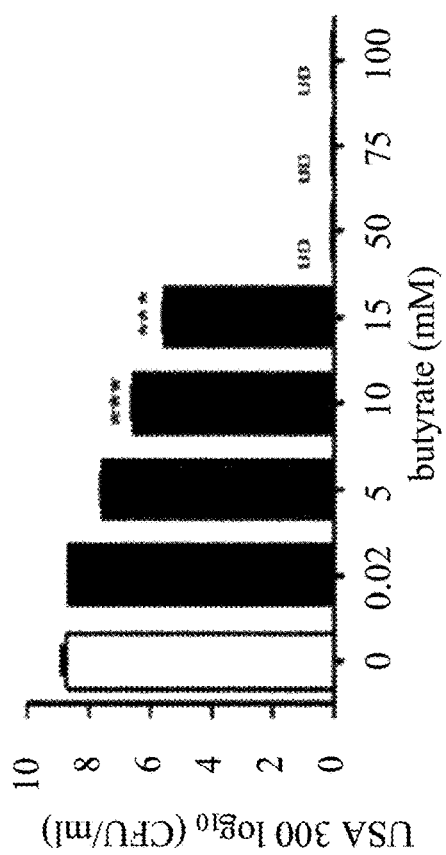
Fig. 4A
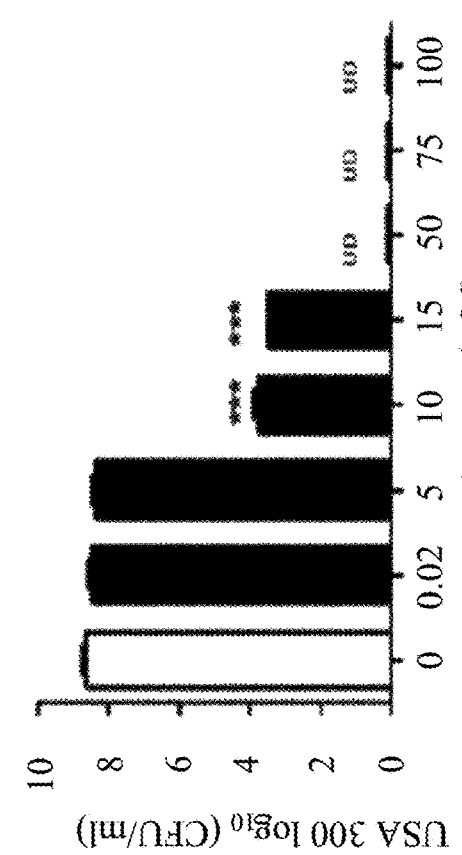
Fig. 4B
Fig. 4C
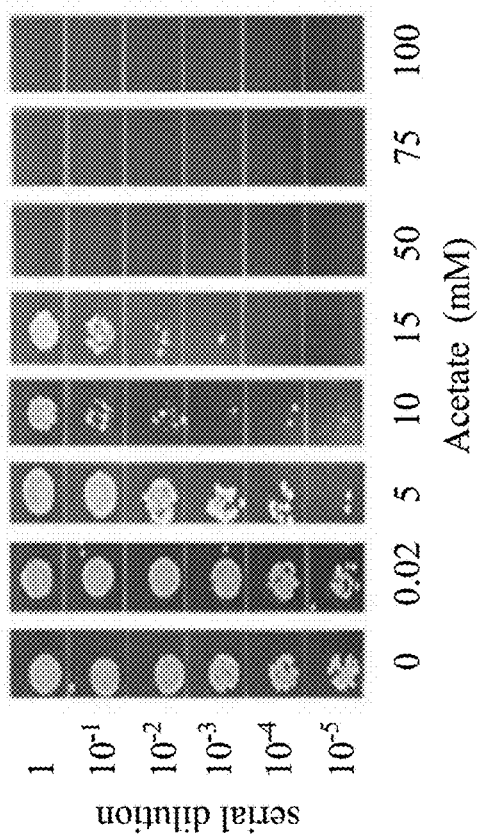
Fig. 4D

BACTERIUM-CONTAINED HYDROGEL AND METHOD OF MAKING THE SAME

CROSS-REFERENCE TO RELATED APPLICATION

This application claims priority to U.S. Provisional Application Ser. No. 62/365,392, filed Jul. 22, 2016, which is herein incorporated by reference.

BACKGROUND

Field of Invention

The present invention relates to a hydrogel. More particularly, the present invention relates to a hydrogel containing bacteria and metabolites of the bacteria.

Description of Related Art

It has been a long time for using fermentation of bacteria to acquire the metabolites of bacteria, for example, culturing lactic acid bacteria, acetic acid bacteria, filamentous bacteria, or actinobacteria. By the enzymes within the bacteria, the substrates in the medium can be converted into primary metabolites, secondary metabolites, or small active molecules, such as ethanol, lactic acid, amino acids, succinic acid, pyruvic acid, or coenzyme Q10.

Most of the metabolic mixtures after fermentation need subsequent processes such as separation, extraction, refining, or purification processes, but these processes may result in the loss of some metabolites. Alternatively, as the physical and chemical properties of some metabolites are unstable, the metabolites tend to violate, degrade, or inactivate. Moreover, if it is necessary to more completely preserve the composition and the activities of the metabolites, high techniques or cost may be required.

SUMMARY

In order to improve the above-mentioned problems, the present disclosure provides a hydrogel, which encapsulates bacteria in a three-dimensional network structure inside the hydrogel, and the bacteria can use the components of the gel body of the hydrogel for fermentation, and the metabolites produced can be directly released from the hydrogel.

One embodiment of the present disclosure provides a bacterium-contained hydrogel, which includes: a hydrogel, which includes a plurality of polymer chains crosslinked with each other, each of the polymer chains include at least one polyethylene glycol chain; bacteria, which are located inside the hydrogel, and the bacteria use the polymer chain as a carbon source for fermentation; and metabolites, which are produced from the fermentation of the bacteria using the polymer chains as a carbon source, and the metabolites are distributed in the hydrogel.

One embodiment of the present disclosure provides a method for preparing a hydrogel, the method includes: providing or receiving an aqueous polymer solution, the aqueous polymer solution containing a polymer having at least one polyethylene glycol chain; mixing bacteria with the aqueous polymer solution containing the polymer having the polyethylene glycol chain; inducing a crosslinking reaction within the aqueous solution containing the bacteria and the polymer having the polyethylene glycol chain, and forming a hydrogel containing the bacteria; and incubating the bacteria in the hydrogel, wherein the bacteria produce metabolites through using the polymer having the polyethylene chain as a carbon source for fermentation.

BRIEF DESCRIPTION OF THE DRAWINGS

FIG. 3A is a spectrum of gas chromatography mass spectrometry analysis according to one experiment.

FIG. 3B is a bar chart of the amounts of short-chain fatty acids according to one experiment.

FIG. 4A shows images of bacterial growth on culture plates according to one experiment.

FIG. 4B shows a bar chart of the bacterial colony numbers according to one experiment.

FIG. 4C shows images of bacterial growth on culture plates according to one experiment.

FIG. 4D is a bar chart of bacterial colony numbers according to one experiment.

DETAILED DESCRIPTION

Figure 1A:
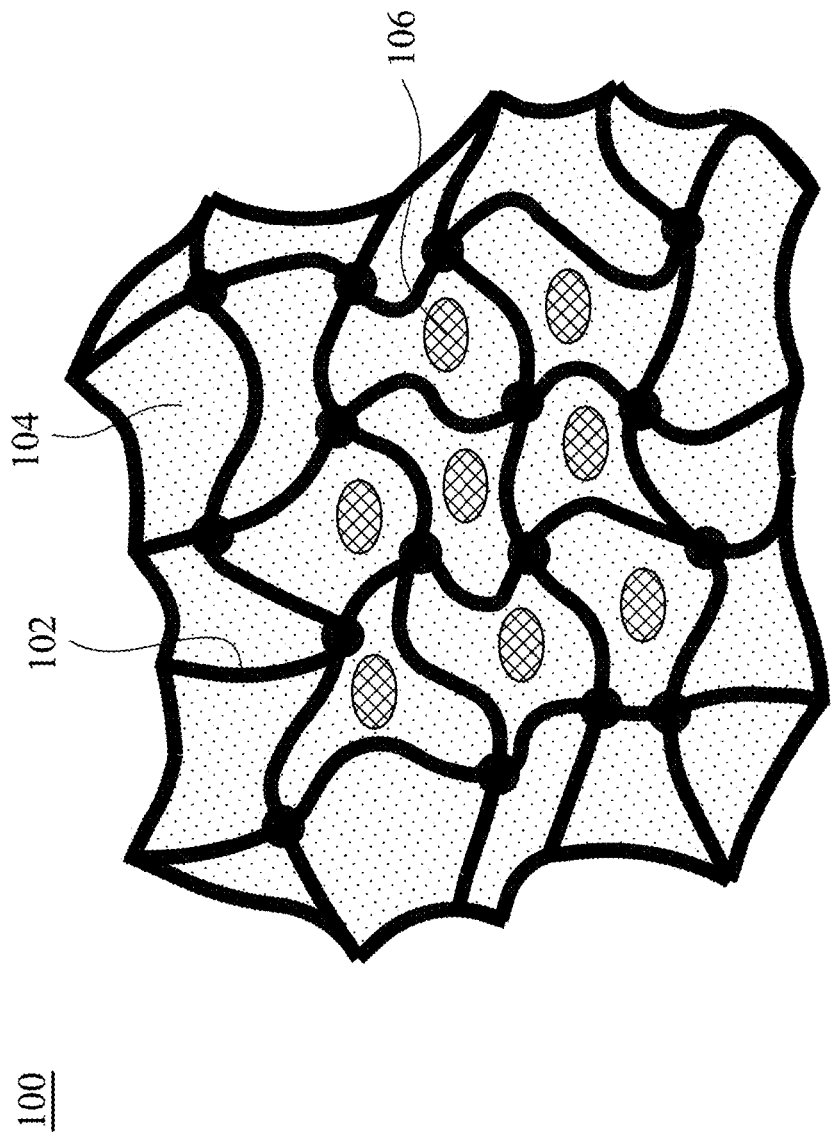
FIG. 1A is a schematic diagram of a hydrogel according to some embodiments.

In order to make the description of the present disclosure more detailed and complete, the following description of the present disclosure and the specific examples is presented with illustrative description; but these embodiments and examples are not the only forms to apply or use the embodiments of the present disclosure. The examples disclosed below may be combined or substituted with each other in a beneficial situation, and other examples may be added to one example without further description or explanation.

In the following description, numerous specific details will be described, so that readers will be able to fully understand the following examples. However, embodiments of the present invention may be practiced without such specific details. For simplicity, well-known structures or devices are illustrated schematically in the drawings. It is noted that the dimensions of the elements in the drawings may be arbitrarily increased or decreased for the clarity of the features in the drawings.

Referring to FIG. 1A, which is a schematic diagram of a hydrogel according to some embodiments, the figure illustrates the structure of a bacterium-encapsulated hydrogel just after formation. The hydrogel 100 is formed by a crosslinking reaction of polymer chains 102, which contains a polyethylene glycol (PEG) chain, and water 104 is inside the hydrogel. Bacteria 106 are encapsulated in the three-dimensional network of hydrogel 100.

Figure 1B:
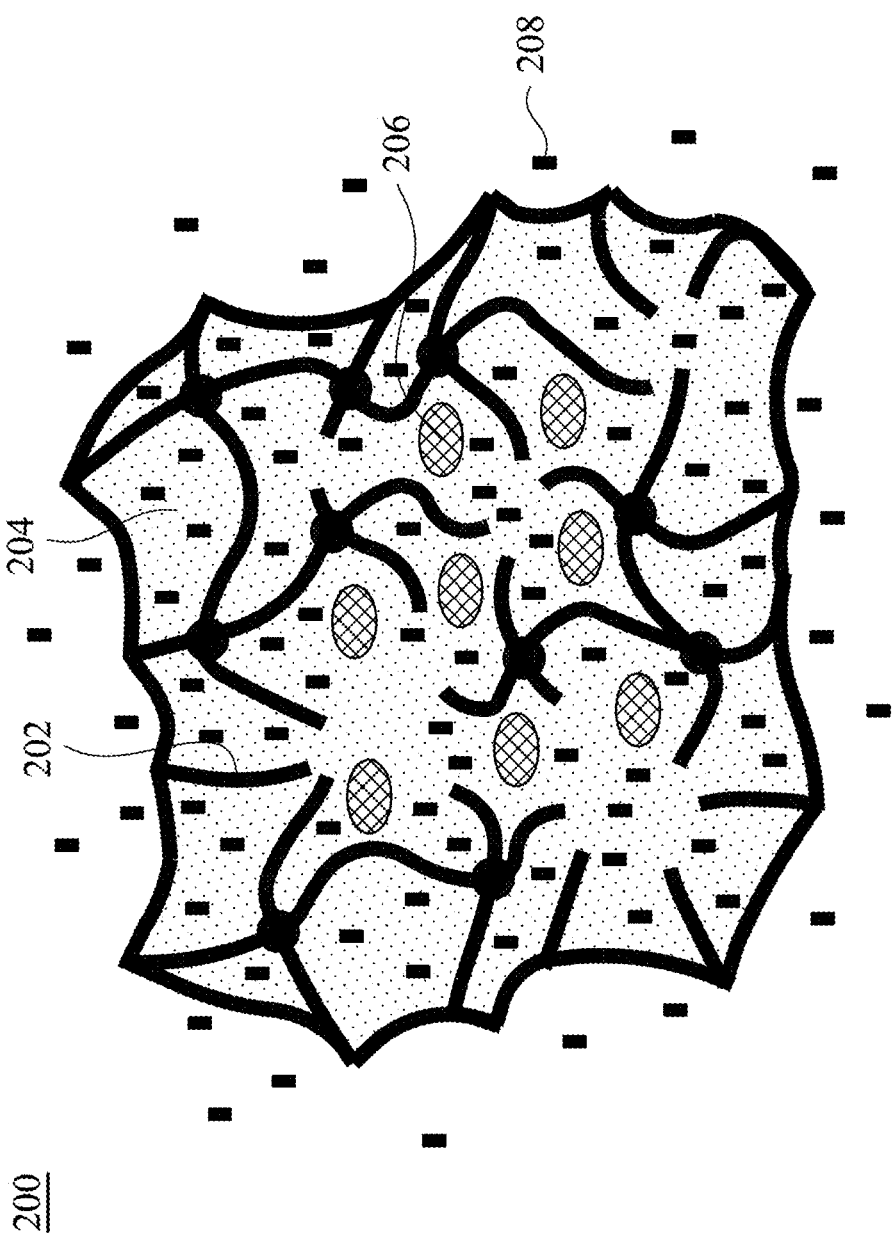
FIG. 1B is a schematic diagram of a hydrogel according to some embodiments.

Referring to FIG. 1B, which is a schematic diagram of a hydrogel according to one embodiment, the figure illustrates the structure of a bacterium encapsulated hydrogel after the initiation of fermentation. Hydrogel 200 is formed by a crosslinking reaction of polymer chains 202, which contain a polyethylene glycol (PEG) chain, and water 204 is inside the hydrogel. Bacteria 206 decompose the polymer chain 202, the polymer chain 202 serving as a carbon source for fermentation, and produce metabolites 208, and some of metabolites 208 may be released to the outside of the hydrogel 200.

Embodiments of the present disclosure use polymers (polymer chains) having a PEG chain to form hydrogels. Polyethylene glycol (PEG) is a water-soluble polyether-type polymer, it has been widely attended in the biomedical application, and it has been recognized by the US Food and Drug Administration (FDA). PEG has many advantages, such as low toxicity, non-coagulation, and biocompatibility. When PEG is crosslinked with other molecules or forms copolymers, many advantages of the excellent properties of PEG will be transferred to the conjugates. Therefore, polymers with PEG base are ideal substrates for hydrogel preparation.

The polymer chains may be PEG or derivatives of PEG. PEG-based hydrogels can be formed from derivatives of PEG by physical or chemical crosslinking reactions, which crosslink the portion of PEG or the terminal groups; therefore, comparing to PEG, derivatives of PEG have more crosslinking ways; accordingly, many hydrogels with different structures and functions can be achieved.

According to some embodiments, polymers having a PEG chain may be polyethylene glycol (PEG), polyethylene glycol dimethacrylate (PEG-DMA), polyethylene glycol diacrylate (PEG-DA), polyethylene glycol methacrylate (PEG-MA), polyethylene glycol diacrylamide (PEG-DAA), or a combination thereof.

According to some embodiments, the molecular weight of the PEG in the polymer may be about 250 to about 10,000, for example, molecular weight of 250, 500, 1000, 2000, 5000, 8000, or 10000.

According to some embodiments, the polymer having a PEG chain may contain a carbohydrate group, a lipid group, or a carboxylic acid group. The carboxylic acid group, the lipid group, and the carbohydrate group are boned to the PEG chain.

According to one embodiment, a polymer having a PEG chain and a carbohydrate group may be Propargyl-PEG5-beta-D-glucose, or PEG5-tetra-Ac-beta-D-glucose.

According to one embodiment, a polymer chain having a PEG chain and a carboxylic acid group is F68-COOH.

According to some embodiments, the hydrogels are formed by crosslinking of different derivatives having a PEG chain; and the hydrogels can be used to screen specific bacterium species which can ferment the hydrogels, or produce different metabolites.

According to one embodiment, the hardness, swelling degree and water content of the hydrogel can be controlled by adjusting the concentration of the polymer chain having a PEG chain in the aqueous solution, or by grafting other carbon-containing molecules.

In some embodiments, for forming a hydrogel with particular shape or thickness, the mixture is injected into a mold before the crosslinking reaction of the polymer chains having a PEG chain. For example, the mold is a U-shape mold composed of glass clamps, silicon strips, and fixing clamps; wherein the silicone strips are placed between the glass clips, and the glass clips are clamped with the silicone strips by fixing clamps.

According to some embodiments, the crosslinking reaction can be induced by adding an initiator, which may be salts of peroxydisulfate, such as sodium peroxydisulfate, potassium peroxydisulfate, or ammonium peroxydisulfate.

According to some embodiments, in preparing the hydrogel, a free radical-generating catalyst may be added, such as, sodium sulfite or tetramethylethylenediamine (N,N,N',N'-tetramethyl-ethane-1,2-diamine, referred to as TEMED).

According to one embodiment, the hydrogel contains an indicator ingredient, such as phenol red, in which the color of the phenol red depends on the pH value in the hydrogel. When the phenol red exhibits a yellow color, it suggests the hydrogel contains acidic bacterial fermentation products.

According to one embodiment, for forming a hydrogel, UV light can be used to initiate the crosslinking reaction of the polymer chain with a PEG chain. For example, polymer chain having a PEG chain (such as PEG-DMA) is dissolved in an aqueous solution, and then a photoinitiator and bacterial liquid are added to the aqueous solution. The PEG-DMA/photoinitiator/bacteria (precursor) are mixed evenly in the dark and injected to a mold. When irradiated the precursor with UV light for the crosslinking reaction, the UV irradiated time do not exceed the time which significantly kill the bacteria, for example, the irradiation time do not exceed 8 minutes. After the illumination of the UV light, the polymer chains having a PEG chain are crosslinked and form a hydrogel, and meanwhile the bacteria are encapsulated in the hydrogel. The photoinitator is a compound which can generate free radicals under light for inducing polymerization.

According to one embodiment, the bacterium species in the hydrogel are commensal bacterium species of a host (e.g., human), for example, *Staphylococcus epidermidis* (*S. epidermidis*) or *Propionibacterium acnes* (*P. acnes*).

According to one embodiment, the bacteria encapsulated in the hydrogel are probiotics. Probiotics are prevalent in the skin, gastrointestinal tract, the upper respiratory tract of a host; the probiotics belong to the normal flora symbiotic with a host, have no or low pathogenicity, and can compete with pathogenic pathogens to improve the balance of the microbial flora of a host; therefore, probiotics are beneficial to the health of a host.

According to one embodiment, the bacteria in the hydrogel have enzymes which can digest PEG chains, for example, diol dehydratase, PEG acetaldehyde lyase, or other enzymes which can decompose polymer chains having a PEG chain. The bacteria may secrete these enzymes to the outside of their body, and convert the PEG chain into metabolic products; alternatively, the bacteria may take in a portion of a polymer chain having a PEG chain, covert the polymer into metabolic products inside the bacteria.

According to some embodiments, the addition of bacteria may be at before the initiation of polymerization, or after the initiation of polymerization but the gel body is not fully solidify.

According to one embodiment, after the bacterial are encapsulated in the hydrogel, the bacteria begin to ferment the PEG-based hydrogel.

According to one embodiment, the bacterium-contained hydrogel can be stored at a lower temperature, for example, 2° C. to 10° C. The hydrogel is stored preferably for 1 to 14 days, more preferably for 1 to 10 days, and further more preferably for to 7 days.

According to one embodiment, the bacterium-encapsulated hydrogels can be placed in liquid culture media to maintain the activity of the bacteria. The temperature for incubating bacteria may be at 20° C. to 40° C., such as 20° C. to 25° C., 25° C. to 30° C., 30° C. to 35° C., and 35° C. to 40° C. The incubating time is 12 hours to 96 hours, preferably 24 to 70 hours, more preferably 48 to 72 hours. The culture media contain carbon source, nitrogen source, sulfur source, phosphorous source, inorganic salt, and trace elements; for example, the culturing medium containing trypsin soy broth (TSB), or Lysogeny broth (LB).

According to one embodiment, in using the PEG-based hydrogen gel (such as covering the surface of skin), the encapsulated bacteria are still alive; therefore, the bacteria continuously ferment and produce metabolites; As a result, the fresh components of the products of the bacteria fermentation can be used, and some easily degradable products are continuously made in the gel body and released.

According to one embodiment, after fermentation and production of metabolites, the hydrogel may be sterilized optionally; for example, by radiation sterilization (such as UV, X-ray, or gamma ray), high temperature steam, chemical treatment (such as alcohol), so that the hydrogel has no bacterial activity before being applied to human body, and the metabolites of fermentation still remain in the hydrogel.

According to one embodiment of the present disclosure, the polymer (polymer chain) having a PEG chain in the hydrogel is a selective fermentation initiator (SFI) of bacteria. In other words, specific bacteria containing enzymes which can decompose and metabolize the polymer chain having a PEG chain can use the hydrogel for fermentation.

According to one embodiment of the present disclosure, the metabolic components released from the hydrogel have beneficial efficacies for the hosts, for example, the components can inhibit the growth of pathogens on the surface or in the mucosa of the hosts.

According to one embodiment, the metabolic products of the hydrogel includes antibacterial substance, such as bacteriocin, or short-chain fatty acids (SCFAs), e.g., acetic acid, propionic acid, butyric acid, isobutyric acid, or isovaleric acid.

The following content illustrates the disclosure of the application through experiments and examples, but the scopes of the claims are not limited by the experiments and examples.

Bacterial Incubation:

Bacteria were cultured in media of tryptic soy broth (TSB) (Sigma, St. Louis, Mo., USA). Overnight cultures were diluted 100 times, and re-cultured to an absorbance at optical density $OD_{600}$ were 1.0. The bacteria were harvested by centrifugation at 5000×g for 10 minutes, washed with phosphate buffered saline (PBS), and suspended in PBS for further experiments.

Experiment 1: Polymers Having a PEG Chain can be a Selective Carbon Source for Bacterial Fermentation Methods: *S. epidermidis* (ATCC No. 12228), *P. acnes* (ATCC No. 6919), and USA300 (a strain of pathogenic *Staphylococcus aureus*) were tested. The three bacteria were respectively cultured in solid media without PEG-DMA, and in solid media with PEG-DMA; then the fermentation status of these strains under different experimental conditions were examined.

Experimental Materials:

1. Preparing rich agar media. The media contain 2% w/v agar, and rich components of medium were added: 10 g/L yeast extract (Biokar Diagnostics, Beauvais, France), 3 g/L TSB, 2.5 g/l K2HPO4, and 1.5 g/l KH2PO4). In addition, 0.002% w/v phenol red was added to the media; the color of phenol red changed from red or red-orange to yellow indicates that acid substance were generated in the media.

2. Preparing media with PEG-DMA. The recipe contains the above mentioned rich agar media and 2% w/v PEG-DMA (number-average Mn=550, catalog number: 25852-47-5, Sigma). The structure formula of PEG-DMA is as follows:

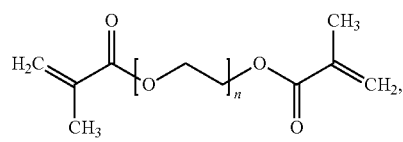

wherein n is the integers corresponding to the molecular weight.

The way for adding the bacteria for testing into the solid media are described as follows: after the agar media were heated and cooled down to 45° C., the bacteria were added and mixed evenly; after the agar media solidified, the bacteria were distributed in the solid media. The amount of the added bacteria was $10^6$ colony-forming units (CFU) per 200 μl solid medium.

The bacteria were cultured in 96-well V-bottom polypropylene (PP) microplate (Corning®, Corning, N.Y.). The volume of solid medium in each well was 200 μl. The control groups included the conditions that the rich agar medium plus only PEG-DMA, or plus only bacteria. The bacteria were incubated at 37° C. for 2 days.

The results of the experiment are shown in the below table 1, wherein "−" means no such component or no bacterium in the culture medium, and "+" means that the component or the bacteria were added into the culture medium. Table 1 shows that, after two days, in the conditions that *S. epidermidis* cultured in medium with PEG-DMA, the color of phenol red in the solid medium turned to yellow. In the conditions that *P. acnes* and USA300 in medium with PEG-DMA, the medium did not be fermented and not turn to yellow. Therefore, PEG-DMA selectively induced the fermentation of *S. epidermidis*, but not *P. acnes* and USA300. Moreover, different bacterium species can produce different enzymes to ferment specific substrates, table 1 shows that among the three bacterium species, *S. epidermidis* has enzymes for PEG-DMA fermentation.

TABLE 1

| | Group 1<br>bacteria(−)<br>PEG-DMA(+) | Group 2<br>bacteria(+)<br>PEG-DMA(+) | Group 3<br>bacteria(+)<br>PEG-DMA(+) |
|---|---|---|---|
| *S. epidermidis* | Red-orange | Red-orange | yellow |
| *P. acnes* | Red-orange | Red-orange | Red-orange |
| USA300 | Red-orange | Red-orange | Red-orange |

Experiment 2 Polymer Having a PEG Chain and a Monosaccharide Group can be a Selective Carbon Source for Bacterial Fermentation The polymers having a PEG chain and a monosaccharide group to be tested are compound A and compound B. Compound A is propargyl-PEG5-beta-D-glucose (molecular weight 394.4), which structural formula is as follows:

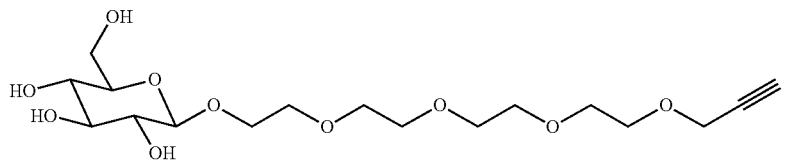 [SMILES: C#CCOCCOCCOCCOCCOC1OC(CO)C(O)C(O)C1O]

Compound B is PEG5-tetra-Ac-beta-D-glucose (molecular weight 562.6), which structural formula is as follows:

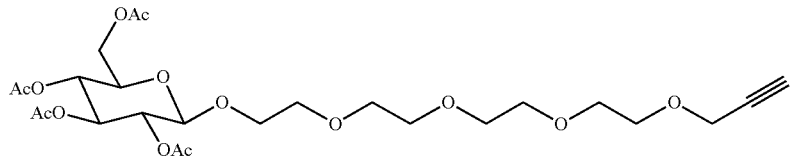 [SMILES: C#CCOCCOCCOCCOCCOC1OC(COC(C)=O)C(OC(C)=O)C(OC(C)=O)C1OC(C)=O]

The experimental method is described as follows: compound A and compound B were respectively added to the solid agar media, and *S. epidermidis* or *P. acnes* were added to the media, then the bacteria were incubated, and then the color of phenol red in the media were recorded.

The results of the experiment are shown in below Table 2, wherein "−" means that no such component in the medium, and "+" means that the component was added in the medium. Table 2 shows that *S. epidermidis* can ferment compound A and compound B, but *P. acnes* cannot ferment compounds A and compounds B. Accordingly, these two polymers having a PEG chain can be a selective fermentation initiator (SFI) of *S. epidermidis*.

TABLE 2

|  | Compound A(−) | Compound A(+) | Compound B(−) | Compound B(+) |
|---|---|---|---|---|
| *S. epidermidis* | Red | Yellow | Red | Yellow |
| *P. acnes* | Red | Red | Red | Red |

Experiment 3 Polymer Having a PEG Chain and a Carboxylic Acid Group can be a Selective Carbon Source for Bacterial Fermentation Poloxamer (F68), also called Poly (ethylene glycol)-block-poly (propylene glycol)-block-poly (ethylene glycol), is a polymer having a PEG chain. The structure formula of F68 (molecular weight 8400, catalog No. 412325, SIGMA-ALDRICH) is as follows:

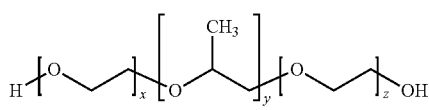

The hydroxyl group (—OH group) at the terminal of F68 were modified to a carboxylic acid (—COOH group), and the structural formula is as follows:

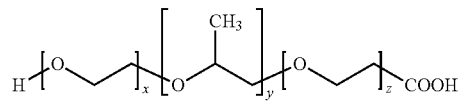

F68 with carboxylic acid (F68-COOH) was added to the TSB liquid medium, and *P. acnes*. were added to the liquid medium and incubated. The below table 3 shows the conditions and results of the experiment, wherein "−" means that no F68-COOH or no bacterium in the liquid medium, "+" means that F68-COOH or bacteria were in the liquid medium.

TABLE 3

| F68-COOH | − | + | − | + |
|---|---|---|---|---|
| *P. acnes* | − | − | + | + |
| Color of the liquid medium after two days | red | Red-orange | red | yellow |

The above results show that when F68-COOH was in the liquid medium, *P. acnes* can metabolize F68-COOH to generate acidic metabolic products. Therefore, for *P. acnes*, F68-COOH is a selective fermentation initiator.

Experiment 4 Double Layers Overlap Assay for Testing the Effect of PEG-DMA Fermentation of *S. epidermidis* on the Growth of USA300

Steps of the experiments are described as follows. Rich agar media were prepared, in which include 2% w/v agar. The media were heated and cool down to 45° C., the USA300 were added; the amount of added bacteria is $10^5$ CFU USA300 per 200 μl medium.

In the experimental group, 2% PEG-DMA was added to the solid media; in the control group, no PEG-DMA was added to the solid media. Bacteria were incubated in 96-well V-bottom PP microplate, and 200 μl medium with USA300 was added to each well. *S. epidermidis* were spread on the upper surface of the solid media having USA300; the amount of *S. epidermidis* for spreading is $10^5$ CFU in 20 μl PBS.

After the bacteria were incubated at 37° C. for two days, the agar image of each culture well was taken and the USA300 colonies (larger than 0.005 mm²) in the solid media were counted by Image J software (NIH, Bethesda, Md., USA).

Figure 2:
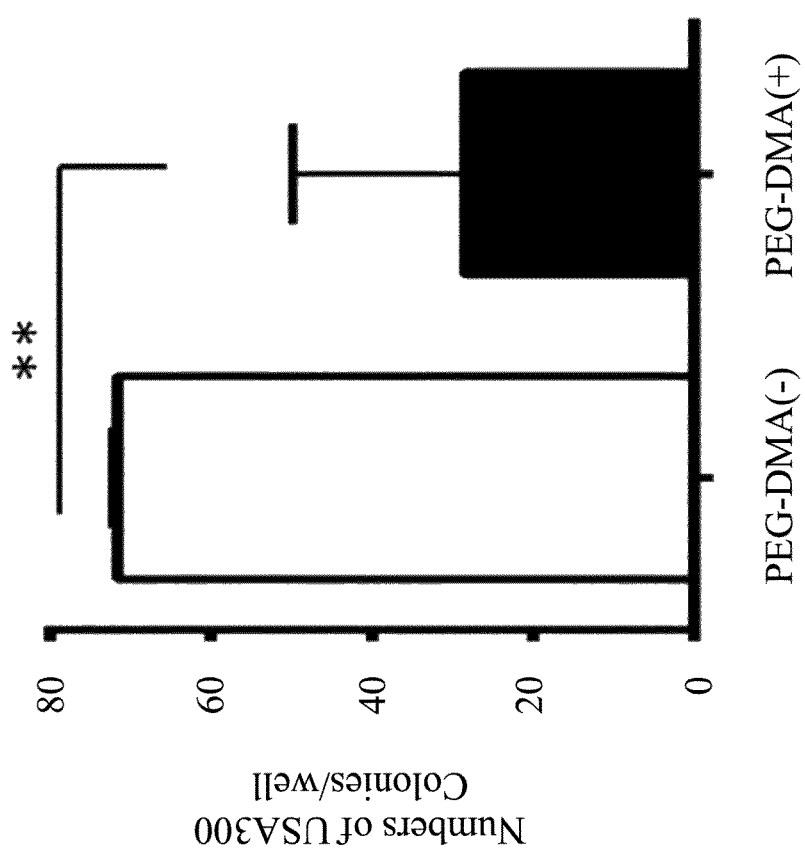
FIG. 2 is a bar chart of bacteria colony numbers according to one experiment.

Referring to FIG. 2, the figure shows the bar chart of the numbers of USA300 colonies in solid media, the numbers are the mean value plus/minus standard derivation (SD) from three independent experiments, the "**" symbol in the figure indicates the p value is less than 0.01 in double tailed t-test.

FIG. 2 shows that the colony numbers of USA300 in media containing PEG-DMA were significantly less than the colony numbers of USA 300 in media without PEG-DMA. Therefore, existence of PEG-DMA can promote the inhibiting USA300 growth effect of S. epidermidis. Moreover, the S. epidermidis on the solid media can ferment PEG-DMA and generate components which can suppress the growth of USA300; the components were diffused into the solid medium, and then diminished the growth of the USA300 colonies inside the solid media.

Experiment 5 Gas Chromatography Mass Spectrometry (GC-MS) Analysis for Media Incubated with S. epidermidis and PEG-DMA The machine for GC-MS assay is Agilent 5890 Series II GC conjugated with 5971 MS detector (Agilent Technologies, Inc., Palo Alto, Calif.).

Experimental steps are described as follows. S. epidermidis (ATCC No. 12228) was cultured in liquid media containing 2% PEG-DMA. In the control group, the liquid media contained no PEG-DMA, and the bacteria were incubated at 37° C. for two days. Then the supernatants were harvested by centrifugation at 5000×g for 10 minutes. The remaining bacteria in supernatants were further removed by 0.22 micron filters. The short-chain fatty acids in the supernatants were detected by gas chromatography-mass spectrometry, and $^2H_7$-butyric acid was an internal standard.

Figure 3C:
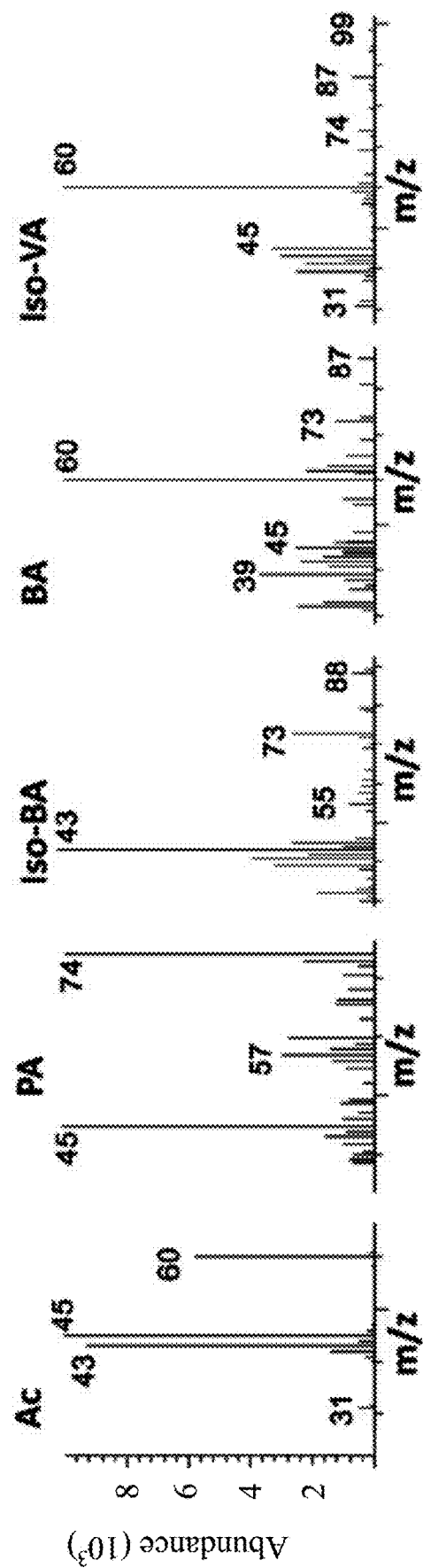
FIG. 3C shows the mass spectra of each of the short chain fatty acids molecules according to one experiment.

Many antibacterial components of bacterial fermentation are short-chain fatty acids; therefore, the components of the short-chain fatty acids of the products of PEG-DMA metabolized by S. epidermidis were analyzed. The results show that, in the supernatants from liquid media without PEG-DMA, only extreme low levels (less than 0.1 μg/ml) of SCFAs were detected. Referring to FIG. 3A, the result of gas chromatography mass spectrometry shows that there were five major SCFAs produced in the PEG-DMA fermentation by S. epidermidis, the SCFAs were acetic acid (Ac), propionic acid (PA), isobutyric acid (Iso-BA), butyric acid (BA), and isovaleric acid (Iso-VA), wherein the "*" symbol represents the peak of the standard ($^2H_7$-butyric acid). Referring to FIG. 3B, which shows a bar chart of the amounts of the SCFAs (unit: micrograms/milliliter). FIG. 3B shows that the sample contained acetic acid (592.1 μg/ml), propionic acid (7.8 μg/ml), isobutyric acid (8.3 μg/ml), butyric acid (3.8 μg/ml), isovaleric acid (11.9 μg/ml). FIG. 3C shows the mass spectra of the five identified short-chain fatty acids (Ac, PA, Iso-BA, BA, and Iso-VA), for example, molecular ions at 31, 43, 45 and 60 m/z respectively corresponding to $NCO^+$, $CH_3CHO^+$, $CH_3CO^+$, and $CH_3COOH$ for acetic acid were detected in a MS spectrum.

These results show that S. epidermidis ferments and metabolizes PEG-DMA to specific components of SCFAs.

Experiment 6 the Minimum Bactericidal Concentration (MBC) Assays for Testing Anti-USA300 Activities of SCFAs Experimental method: USA 300 ($10^6$ CFU/m L) were respectively incubated with different concentrations of butyric acid or acetic acid on 96-well microtiter plates overnight; the testing concentrations of acetic acid and butyric acid were from 0.02 mM to 100 mM, each well was respectively added 100 microliters of acetic acid or butyric acid with different concentrations. In the control groups, only PBS was added to the wells. After incubation, the USA300 was diluted $1:10^0$ to $1:10^5$ with PBS, 5 μl of the dilution was spread to the agar plate; after overnight incubation, colonies (CFU) on the algal plate were counted. MBC is defined as the degree of sterilization at 99.9% (greater than one $\log_{10}$ colony/mL).

Referring to FIG. 4A through FIG. 4D. FIG. 4A and FIG. 4C show the images of bacterial growth on culture plates. FIG. 4B and FIG. 4D are bar chars of quantification results according to three independent experiments, and the figures show the mean value plus/minus standard derivation. The symbol "***" indicates that the p-value is less than 0.001 in two-tailed t-test. UD means undetectable.

The results show that the MBC value of butyric acid and the MBC value of acetic acid were 10 mM, and the concentration of the two acids for complete inhibition was 50 mM.

It has been known that Propionic acid can suppress the growth of USA300 in vitro and in vivo. The anti-USA300 activity of propionic acid is derived from its ability to reduce the intracellular pH of USA300. In the experiment, since acetic acid and butyric acid are two of the most abundant SCFAs in the media of PEG-DMA fermentation of S. epidermidis, the anti-USA300 activities of acetic and butyric acid were examined in vitro and in vivo in this experiment. The results show that these two short chain fatty acids had excellent efficacy of anti-USA300 growth.

Experiment 7 S. epidermidis Encapsulated in PEG-DMA Hydrogel can Ferment PEG-DMA Hydrogel fabrication method: 10% weight/volume (w/v) of PEG-DMA (number-average Mn=550, catalog number: 25852-47-5, Sigma) were dissolved in water, then 0.002% w/v of phenol red was added for serving as an indicator, 0.001% of ammonium peroxydisulfate was added to serve as an initiator of free radicals, and S. epidermidis ($2×10^8$ CFU/mL) were added to the mixture, then components were mixed evenly. Then TEMED was added to the mixture for serving as a catalyst for free radical reaction, TEMED induced the crosslinking reaction of PEG-DMA to form hydrogels and S. epidermidis were encapsulated in the hydrogels. Moreover, the hydrogel gels of control groups were prepared, for example, hydrogels without S. epidermidis, acrylamide hydrogels without S. epidermidis, and acrylamide hydrogels encapsulating S. epidermidis.

Then the hydrogels were placed in liquid media containing TBS, and were incubated at 37° C. for three days.

Table 4 shows that the colors of hydrogels after two days of incubation; the color of phenol red relates to the fermentation reaction inside the hydrogel. The symbol "−" means that there was no S. epidermidis in the hydrogel, and the symbol "+" means that there were S. epidermidis encapsulated in the hydrogel. Table 4 shows that in the conditions of PEG-DMA hydrogel encapsulating S. epidermidis, the color of the phenol red in hydrogels changed from red-orange to yellow; meanwhile, acrylamide hydrogels and hydrogels without S. epidermidis did not show this phenomenon. Therefore, S. epidermidis can metabolize PEG-DMA inside the hydrogel.

TABLE 4

|  | S. epidermidis (−) | S. epidermidis(+) |
| --- | --- | --- |
| PEG-DMA hydrogel | Red-orange | Yellow |
| Acrylamide hydrogel | Red-orange | Red-orange |

Experiment 8 PEG-DMA Hydrogel Encapsulating S. epidermidis can Suppress USA 300 in Skin Wounds in Mice Experiments involving mice were performed at the University of California, San Diego (UCSD). The UCSC ethics committee approved this study under an approved Institutional Animal Care and Use Committee (IACUC) protocol (no. S10058).

Hydrogel fabrication method: 10% weight/volume (w/v) of PEG-DMA (number-average Mn=550, catalog number: 25852-47-5, Sigma) were dissolved in water, 0.001% of ammonium peroxydisulfate was added for serving as an initiator of free radicals, and S. epidermidis ($2 \times 10^8$ CFU/mL) was added, then the components were mixed evenly. Then TEMED was added for serving as a catalyst for free radical reaction, TEMED induced the crosslinking reaction of PEG-DMA to form hydrogels and S. epidermidis were encapsulated in the hydrogels. Then the hydrogels were placed in liquid media with TBS. In addition, PEG-DMA hydrogels without S. epidermidis, acrylamide hydrogels without S. epidermidis, and acrylamide hydrogels encapsulating S. epidermidis were prepared.

Animals in the experiment were Institute of Cancer Research (ICR) mice (2 to 3 months-old female) (Harlan Labs, Placentia, Calif., USA). The mice were anesthetized with isoflurane, two 1 mm wounds were respectively made on the left and right sides of the dorsal skin of the mice by electric scissors; the wounds are the first wound, and the second wound, respectively. To recapitulate the infection of methicillin-resistant Staphylococcus aureus (MRSA), the buffer with USA300 ($10^8$ CFU dissolved in 10 µl PBS) was applied to the wounds.

In the experiment group, 10 minutes after the mice were infected with USA300, a PEG-DMA hydrogel (without S. epidermidis) was applied over the first wound, and a PEG-DMA hydrogel encapsulating S. epidermidis was applied over the second wound of the same mouse.

In the control group 1, 10 minutes after the mice were infected with USA300, the first wound was not covered with hydrogel, and the second wound of the same mouse was covered with PEG-DMA hydrogel (without S. epidermidis).

In the control group 2, 10 minutes after the mice were infected with USA300, acrylamide hydrogel (without S. epidermidis) was applied over the first wound, and acrylamide hydrogel encapsulating S. epidermidis was applied over the second wound of the same mouse.

The experiment was performed three times independently; the mouse number in each group of every experiment is three. All experiments using mice were conducted in a biosafety level 2 (BSL-2) facilities.

To determine the USA300 counts, the infected wounds were excised 24 hours following infection of USA300. The excised skin was homogenized in 500 µl PBS with a tissue grinder. The tissue homogenates were serially diluted, then were spread on a phenol-red supplemented mannitol salt agar (MSA) plate (BD, Sparks, Md., USA). The plates were incubated at 37° C. for 24 hours, and then the colonies on the plates were counted, wherein the yellow colonies were recognized as USA300 colonies.

Figures 5A, 5B:
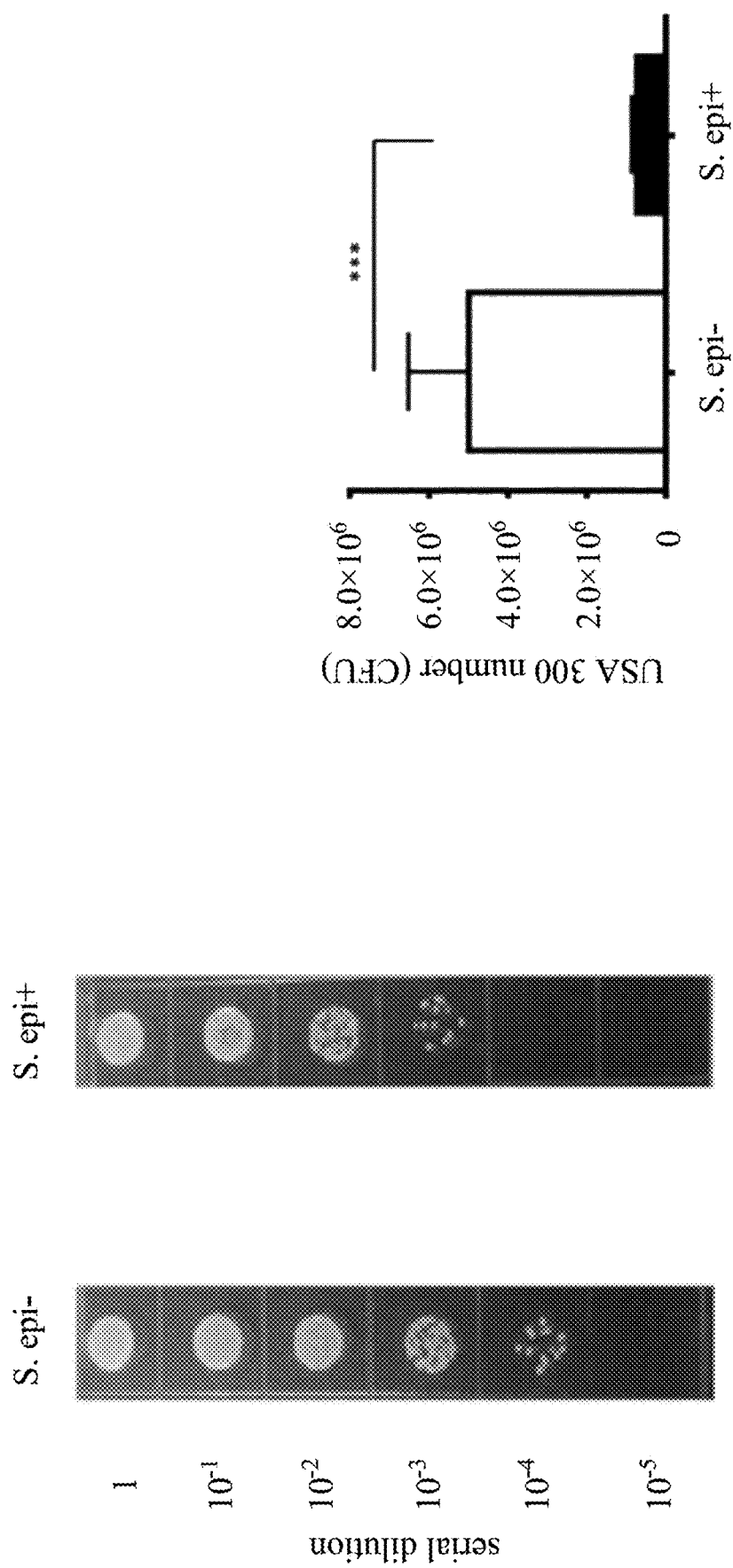
FIG. 5A shows images of bacterial growth on culture plates according to one experiment.
FIG. 5B is a bar chart of bacterial colony numbers according to one experiment.
Figures 5C, 5D:
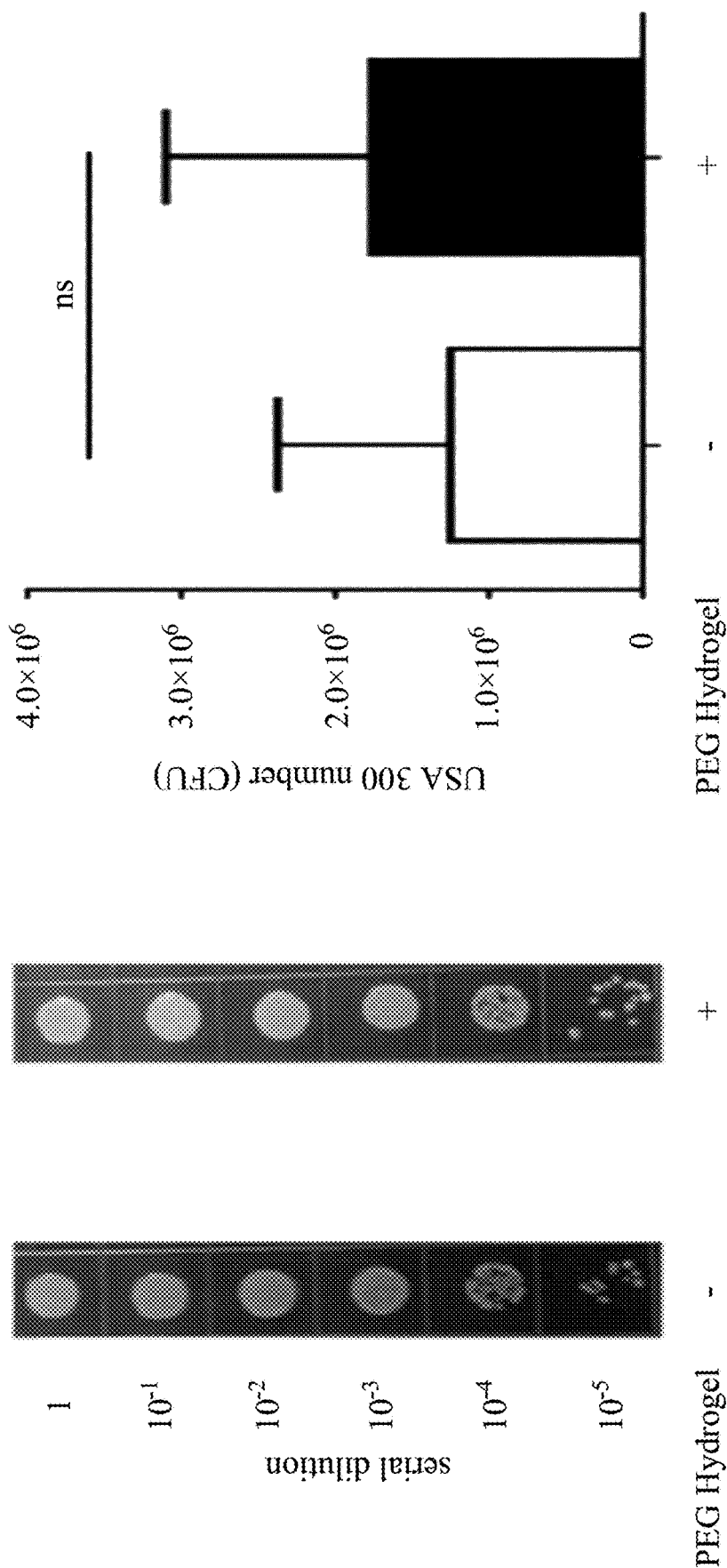
FIG. 5C shows images of bacterial growth on culture plates according to one experiment.
FIG. 5D is a bar chart of bacteria colony numbers according to one experiment.
Figures 5E, 5F:
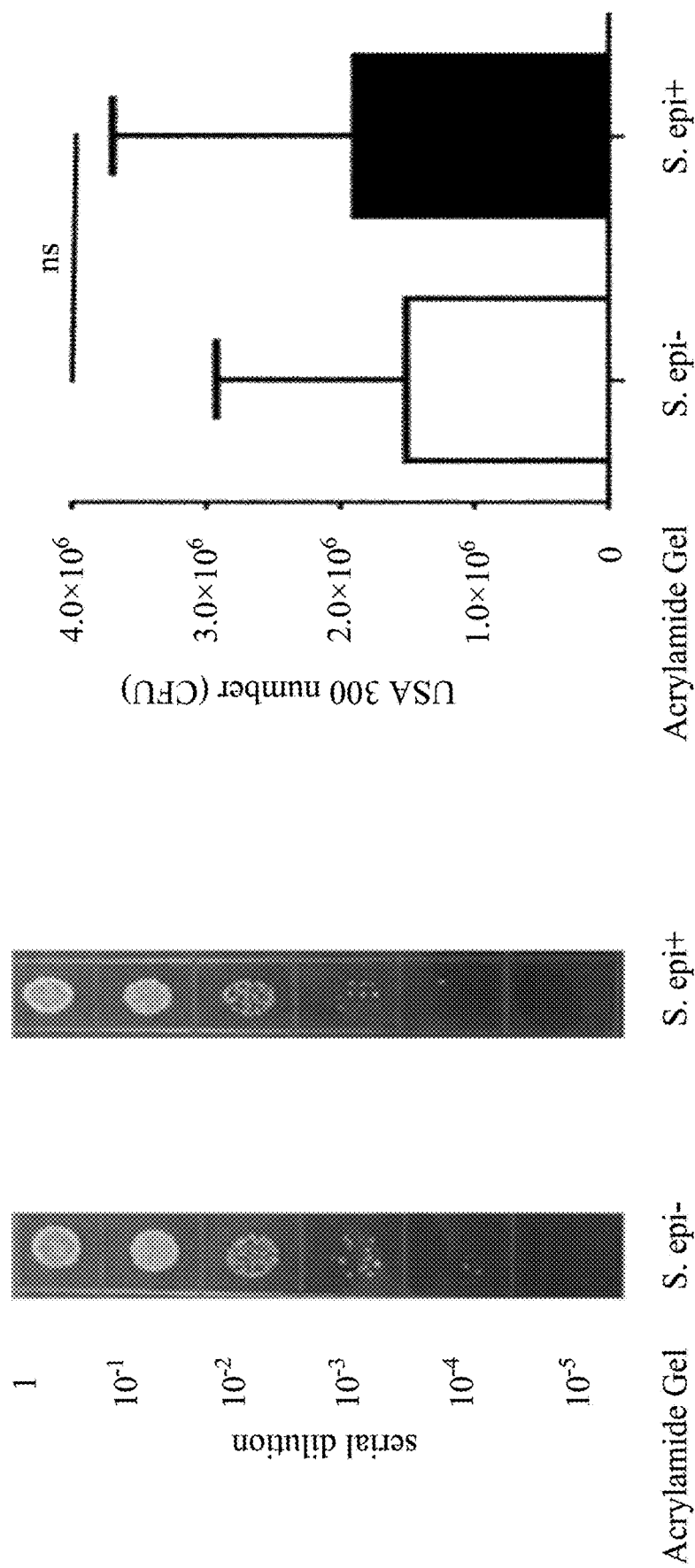
FIG. 5E shows images of bacterial growth on culture plates according to one experiment.
FIG. 5F is a bar chart of bacteria colony numbers according to one experiment.

Referring to FIG. 5A through FIG. 5F, in which FIG. 5A, FIG. 5C, and FIG. 5E are images of bacterial growth at different serial dilution concertation. FIG. 5B, FIG. 5D, and FIG. 5F are the quantification results from three independent experiments, wherein the mouse number of each group is three. The figures show the average colony numbers plus/minus standard derivation of USA300 (yellow colony). The symbol "***" indicates that the p-value is less than 0.001 in two-tailed t-test.

FIG. 5A and FIG. 5B show that the number ($7.5 \pm 1.2 \times 10^5$ CFU) of USA300 in the wound covered by a PEG-DMA gel with S. epidermidis was significantly less than that ($5.0 \pm 1.5 \times 10^5$ CFU) in the wound covered by a PEG-DMA-hydrogel without S. epidermidis. The results demonstrate that PEG-DMA hydrogel encapsulating S. epidermidis possess the probiotics activity against USA300 in wounds.

FIG. 5C and FIG. 5D show the experiment results of control group 1, PEG-DMA hydrogel did not diminish the growth of USA300 in wounds; the result means that PEG-DMA hydrogel per se did not affect the colonization of USA300 in wounds. The symbol "ns" in FIG. 5D means the statistical result is not significant.

FIG. 5E and FIG. 5F show the experiment results of control group 2, for the growth of the USA300 in wounds, there was no significant difference between the acrylamide gel containing S. epidermidis. and the acrylamide gel containing no S. epidermidis. The symbol "ns" in the FIG. 5F means the statistical result is not significant.

The above results show that after PEG-DMA fermentation in the hydrogel, the hydrogel has efficacy of inhibiting the growth of pathogen USA300 in wounds.

The efficacies of the present disclosure:

The hydrogel of the present disclosure can maintain a large amount of water in the three-dimensional structure of the gel body, and can maintain a fixed shape; therefore, the hydrogel is used as a carrier to provide or maintain the humidity of the covered site, and to slowly release active molecules from the hydrogel.

The PEG-based hydrogel in the present disclosure can be a carbon-rich microenvironment, which can not only for bacteria to survive in, but it also can induce bacteria to use polymer having a PEG chain as a carbon source for fermentation, and release functional products of fermentation. For example, the results of the experiments of the present disclosure show that PEG-DMA encapsulating S. epidermidis specifically ferment and metabolize PEG-DMA into specific SCFAs, and the hydrogel has excellent antibacterial activity. SCFAs are fatty acids generally contain two to six carbons, and they are also called as volatile fatty acids; SCFAs are volatile compounds with short half-life and can be metabolized quickly. SCFAs not only can inhibit the growth of pathogenic bacteria, but they can also be inhibitors of class I and class II histone deacetylase (HDAC); furthermore, they can inhibit inflammation reactions.

Accordingly, one of the uses of the hydrogel of the present disclosure is a novel antibacterial hydrogel for application in biomedical field, such as for skin care products (e.g., masks, gels), or for medical materials (e.g., dressing, patch).

Different bacterium species in hosts can produce different specific enzymes to metabolize specific carbon sources. Most of the skin commensal bacteria include S. epidermidis, P. acnes, and pathogenic S. aureus; these bacteria can metabolize the same carbon source such as glucose to SCFAs. To gain maximum chances to survive, commensal bacteria and pathogenic bacteria may exclude each other via production of SCFAs by fermentation of glucose. When S. aureus survives after the bacterial interference, the infection will proceed to continue to damage the host. Examples of the present disclosure show that the fermentation of S. epidermidis is specifically triggered by a SFI; therefore, the probiotic effect of S. epidermidis against pathogenic S. aureus can be amplified.

Methicillin-resistant S. aureus (MRSA), or multiple-resistant S. aureus, is a unique strain of S. aureus and it is resistant to almost all penicillin antibiotics including Methicillin and other anti-β-lactamase Penicillin. MRSA was first discovered in 1961 in UK and is now widely distributed, and in hospital the strain of bacteria is called "super bacteria".

Although an incision and drainage procedure was performed for the majority of MRSA-infected patients, antibiotics are usually given as adjunctive therapy. However, through antibiotics for MRSA treatment, the bacteria may evolve abilities to neutralize the antibiotics. In other words, the use of antibiotics increases the risk of generating resistant bacteria and non-specifically kills commensal bacteria of hosts.

The hydrogel of the present disclosure can be applied as an adjuvant to reduce the amounts of antibiotics in antibiotics treatment; therefore, the chance of generating resistant bacteria is reduced, and the killing effect for nonpathogenic commensal bacteria is also reduced.

The hydrogel of the present disclosure can be applied to the patch formulation of transdermal administration. The delivering system of transdermal administration can slowly release functional molecules in a long term. However, some functional secondary metabolites of bacteria have short half-life; hence, the functional molecules can be continuously produced and released by fermentation of bacteria inside the gel body.

Although the present invention has been described in considerable detail with reference to certain embodiments thereof. The appended claims should not be limited to the description of the embodiments contained herein. It will be apparent to those skilled in the art that various modifications and variations can be made without departing from the scope or spirit of the invention. Therefore, the scopes of the claims depend on what defined in the claims.

What is claimed is:

1. A bacterium-contained hydrogel comprising:
   a hydrogel comprising a plurality of polymer chains crosslinked with each other, wherein the polymer chains are PEG-DMA, lipid group-bonded PEG chains, or carbohydrate group-bonded PEG chains;
   bacteria located within the hydrogel, wherein the bacteria are *Staphylococcus epidermidis*, and the *Staphylococcus epidermidis* use the polymer chains as a carbon source for fermentation; and
   metabolites produced from the fermentation of the *Staphylococcus epidermidis* using the polymer chains as the carbon source, wherein the metabolites distribute in the hydrogel.

2. The bacterium-contained hydrogel of claim 1, wherein a molecular weight of each of the polymer chains is about 250 to about 10000.

3. The bacterium-contained hydrogel of claim 1, wherein the metabolites comprise a short chain fatty acid having two to six carbon atoms.

4. A bacterium-contained hydrogel comprising:
   a hydrogel comprising a plurality of polymer chains crosslinked with each other, wherein the polymer chains are carboxylic acid group-bonded PEG chains;
   bacteria located within the hydrogel, wherein the bacteria are *Propionibacterium acnes*, and the *Propionibacterium acnes* use the carboxylic acid group-bonded PEG chains as a carbon source for fermentation; and
   metabolites produced from the fermentation of the *Propionibacterium acnes* using the carboxylic acid group-bonded PEG chains as the carbon source, wherein the metabolites distribute in the hydrogel.

5. A method for preparing a bacterium-contained hydrogel comprising:
   providing or receiving an aqueous polymer solution, the aqueous polymer solution containing polymer chains having at least one polyethylene glycol chain, wherein the polymer chains are PEG-DMA, lipid group-bonded PEG chains, or carbohydrate group-bonded PEG chains;
   mixing bacteria with the aqueous polymer solution containing the polymer chains having the polyethylene glycol chain; wherein the bacteria are *Staphylococcus epidermidis*;
   inducing a crosslinking reaction within the aqueous solution containing the bacteria and the polymer chains having the polyethylene glycol chain, and forming a hydrogel containing the bacteria; and
   incubating the bacteria in the hydrogel, wherein the bacteria produce metabolites through using the polymer chains having the polyethylene chain as a carbon source for fermentation.

6. The method for preparing the bacterium-contained hydrogel of claim 5, wherein inducing the crosslinking reaction within the aqueous solution containing the bacteria and the polymer chains having the polyethylene glycol chain comprises:
   adding ammonium peroxydisulfate and tetramethylethylenediamine (TEMED) in the aqueous polymer solution containing the bacteria and the polymer chains having the polyethylene glycol chain.

7. The method for preparing the bacterium-contained hydrogel of claim 6, wherein a molecular weight of each of the polymer chains is about 250 to about 10,000.

8. The method for preparing the bacterium-contained hydrogel of claim 5, wherein inducing the crosslinking reaction within the aqueous solution containing the bacteria and the polymer chains having the polyethylene glycol chain comprises:
   adding a photoinitiator to the aqueous polymer solution containing the bacteria and the polymer chains having the polyethylene glycol chain, and forming a precursor; and
   irradiating the precursor by ultraviolet light.

9. The method for preparing the bacterium-contained hydrogel of claim 5, wherein the metabolites comprise a short chain fatty acid having 2 to 6 carbon atoms.

10. The method for preparing the bacterium-contained hydrogel of claim 5, the method further comprising incubating the bacterium-contained hydrogel in a medium with nutrients.

* * * * *